US00PP34280P2

(12) United States Plant Patent
Thiede

(10) Patent No.: US PP34,280 P2
(45) Date of Patent: May 31, 2022

(54) ***DIANTHUS* PLANT NAMED 'KLEDG22998'**

(50) Latin Name: ***Dianthus* x *allwoodii***
Varietal Denomination: KLEDG22998

(71) Applicant: Klemm+Sohn GmbH & Co. KG, Stuttgart (DE)

(72) Inventor: Lena Thiede, Riederich (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/517,932

(22) Filed: Nov. 3, 2021

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 5/02
See application file for complete search history.

(56) References Cited

PUBLICATIONS

CPVO Citation for 'KLEDG22998' as per PBR QZ 20212558; Oct. 12, 2021; 2 pages.*

* cited by examiner

*Primary Examiner* — Kent L Bell
(74) *Attorney, Agent, or Firm* — Weatherly IP Solutions, LLC; James M. Weatherly

(57) ABSTRACT

A new *Dianthus* plant named 'KLEDG22998' particularly distinguished by a double flower with a pink and purple boarder with a red center and a very early time to flower.

1 Drawing Sheet

Genus and species: *Dianthus* x *allwoodii.*
Variety denomination: 'KLEDG22998'.

BACKGROUND OF VARIETY 'KLEDG22998'

The present invention comprises a new and distinct variety of *Dianthus*, botanically known as *Dianthus* x *allwoodii* and hereinafter referred to by the variety name 'KLEDG22998'. 'KLEDG22998' is a selection that resulted as a whole plant mutation of the commercial *Dianthus* line 'KLEDG12163' (U.S. Plant Pat. No. 24,707).

In May 2018, a whole plant mutation of 'KLEDG12163' was discovered and selected in Stuttgart, Germany, and named 'KLEDG22998'. 'KLEDG22998' was found to reproduce true to type in successive generations of asexual propagation via vegetative cuttings in Stuttgart, Germany.

SUMMARY OF VARIETY 'KLEDG22998'

The following are the most outstanding and distinguishing characteristics of this new variety when grown under normal horticultural practices in Stuttgart, Germany.

1. Double flower with a pink, purple border and red center; and
2. A very early time to flower.

DESCRIPTION OF THE PHOTOGRAPH

This new *Dianthus* plant is illustrated by the accompanying photograph which shows the overall plant habit of the variety 'KLEDG22998' grown in a pot. The photograph is of a 30-week-old plant in Stuttgart, Germany grown in a greenhouse in May 2019.

DESCRIPTION OF THE NEW VARIETY 'KLEDG22998'

The following detailed descriptions set forth the distinctive characteristics of 'KLEDG22998'. Data was collected on seven-month-old plants potted and cultivated indoors in Stuttgart, Germany in April of 2021. Color references are to The R.H.S. Colour Chart of The Royal Horticultural Society of London (R.H.S.), 5$^{th}$ edition.

Classification:
*Family.*—Caryophyllaceae.
*Species.*—*Dianthus* x *allwoodii.*
*Common name.*—Pot carnation.

Parentage:
*Female parent.*—The mutation of *Dianthus* 'KLEDG12163' (U.S. Plant Pat. No. 24,707).
*Male parent.*—Not applicable.

Propagation:
*Propagation type.*—Vegetative via stem, terminal cuttings.
*Time to produce a rooted young plant.*—10 to 14 days.
*Root description.*—Young roots: RHS 161D. Mature roots: RHS 199C.
*Rooting habit.*—Lanceolate.

Plant description:
*Form.*—Upright.
*Height.*—15.0 cm to 17.0 cm.
*Diameter or spread.*—22.0 cm to 25.0 cm.

Lateral branches:
*Length.*—7.0 cm to 10.0 cm.
*Diameter.*—4.0 cm to 7.0 cm.
*Internode length.*—2.0 cm to 3.0 cm.
*Number of internodes per branch/stem.*—3 to 5.
*Node length.*—0.2 cm to 0.4 cm.

*Node diameter.*—0.2 cm to 0.4 cm.
*Texture.*—Smooth.
*Color.*—RHS 146B.

Foliage description:
*Arrangement.*—Opposite.
*Length.*—4.0 cm to 5.0 cm.
*Width.*—0.3 cm to 0.5 cm.
*Shape.*—Lanceolate.
*Apex.*—Acute.
*Base.*—Obtuse.
*Margin.*—Entire.
*Texture.*—Upper and lower surfaces: Smooth.
*Immature leaf color.*—Upper surface: RHS 138A. Lower surface: RHS 138A.
*Mature leaf color.*—Upper surface: RHS 137A. Lower surface: RHS 137A.
*Venation pattern.*—No venation.

Flower description:
*Flower type and habit.*—Double, small sprays, round.
*Fragrance.*—Present.
*Natural flowering season.*—Spring to Autumn.
*Position of flowers relative to the foliage.*—Moderately above foliage.
*Number of flowers per spray.*—3 to 5.
*Flower longevity on the plant.*—14 to 18 days.
*Flower buds.*—Length: 0.5 cm to 1.5 cm. Diameter: 0.3 cm to 0.4 cm. Shape: Elliptic. Color: RHS 138A. Extrusion of the styles at the bud stage: Absent.
*Corolla.*—Quantity of petals and arrangement: 7 to 13, average of several whorls. Corolla height: 0.8 cm to 1.5 cm. Petal length: 1.8 cm to 2.5 cm. Petal width: 1.0 cm to 1.5 cm. Petal shape: Spoon shaped. Petal apex: Obtuse. Petal base: Acute. Petal margin: Serrated. Depth of petal margin: Shallow. Petal texture: Upper and lower surfaces: Smooth. Petal color: Immature: Upper surface: RHS 61A and RHS 68D border. Lower surface: RHS 69A. Mature: Upper surface: RHS 61A and RHS 68D border. Lower surface: RHS 69A. Calyx: Quantity of sepals and arrangement: Composed of 5 sepals. Shape: Campanulate. Calyx height: 0.8 cm to 1.5 cm. Calyx diameter (at the apex): 0.4 cm to 0.6 cm. Sepal texture: Upper and lower surfaces: Smooth. Sepal color: Upper surface: RHS 137A. Lower surface: RHS 137D.

Peduncles:
*Length.*—5.0 to 8.0 cm.
*Diameter.*—0.2 cm.
*Strength.*—Moderate.
*Texture.*—Smooth.
*Color.*—RHS 146B.

Reproductive organs:
*Stamens.*—Quantity per flower: Moderate. Filament length: 0.5 cm to 0.8 cm. Filament color: RHS 157B. Anther length: 0.1 cm. Anther diameter: 0.05 cm. Anther color: RHS 155B. Pollen amount: Absent.
*Pistils.*—Not observed.

Fruit and seed set: Seed sometimes observed but information not available.

Disease and insect/pest resistance: No special observations were made. cl COMPARISON OF 'KLEDG22998' WITH PARENTAL LINE AND KNOWN VARIETY When 'KLEDG22998' is compared to the female parental line, the following differences are noted in Table 1:

TABLE 1

Comparison with Parental and Commercial Line

| Trait or characteristic | 'KLEDG22998' | Female parent |
|---|---|---|
| Main flower color | RHS 61A | RHS 75B |
| Second flower color | RHS 68D | RHS 71A |
| Flower color pattern | Border | Bicolor |

When 'KLEDG22998' is compared to the commercial line 'KLEDG18305' (U.S. Plant Pat. No. 31,019), the following differences are noted in Table 2:

TABLE 2

Comparison with Similar Variety

| Trait or characteristic | 'KLEDG22998' | Commercial line: 'KLEDG18305' |
|---|---|---|
| Flower type | Double | Single |
| Flower color | Pink, purple red center | Pink with purple ring |
| Flowering time | Very early | Early-medium |

I claim:

1. A new and distinct variety of *Dianthus* plant named 'KLEDG22998' as shown and described herein.

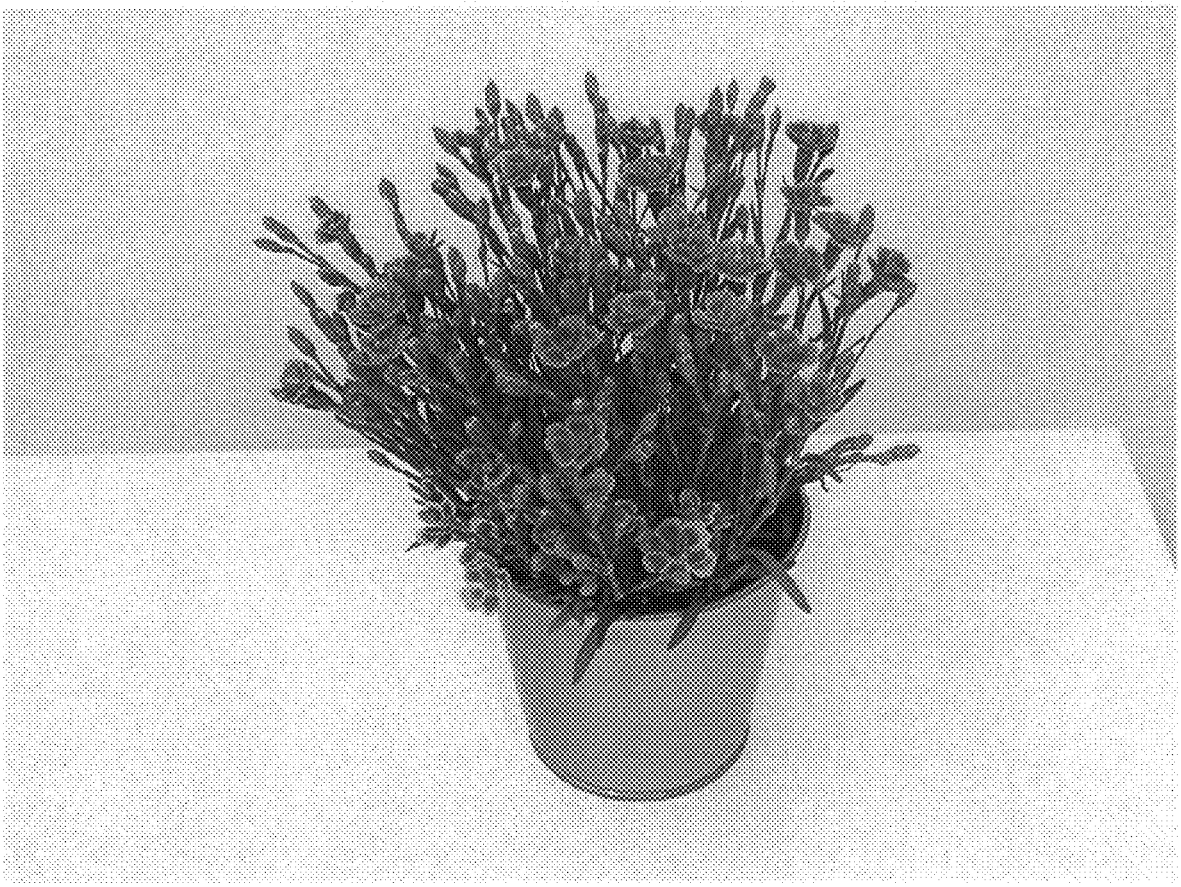

* * * * *